United States Patent [19]

Barker

[11] Patent Number: 4,538,601
[45] Date of Patent: Sep. 3, 1985

[54] KIT FOR AND METHOD OF IMMOBILIZING THE CERVICAL SPINE

[76] Inventor: A. Paul Barker, 2701 S. 13th St., Arlington, Va. 22204

[21] Appl. No.: 543,836

[22] Filed: Oct. 20, 1983

[51] Int. Cl.³ ............................................... A61F 5/04
[52] U.S. Cl. ................................................. 128/89 R
[58] Field of Search ................. 128/87 R, 87 B, 89 R, 128/90, 75, DIG. 20, 132 R, 76 R

[56] References Cited

U.S. PATENT DOCUMENTS

| | | |
|---|---|---|
| 2,947,307 | 8/1960 | Hoppe . |
| 3,301,252 | 1/1967 | Mahoney . |
| 3,419,506 | 12/1968 | Gander . |
| 3,563,234 | 2/1971 | Umstead . |
| 3,572,330 | 2/1971 | Gander . |
| 3,765,412 | 10/1973 | Ommaya et al. ............ 128/DIG. 20 |
| 4,161,946 | 7/1979 | Zuesse ......................... 128/DIG. 20 |
| 4,309,990 | 1/1982 | Brooks et al. . |

Primary Examiner—John D. Yasko
Attorney, Agent, or Firm—Robbins & Laramie

[57] ABSTRACT

The present invention describes a kit which contains two components to immobilize the cervical spine and a method for immobilizing the cervical spine. The first component comprises straps, preferably at least two straps, each strap having a first portion which engages certain body parts and a second portion which engages the second component such that the strap becomes anchored to the second component. The second component is a substance which can be extruded from a container in a semisolid state and which can mold to the contours of objects before hardening into a rigid solid state. To immobilize the cervical spine, the straps of the first component are held in place on, by way of example, the chin and forehead, while the second component is applied to the areas of the anterior, superior and posterior aspects of the shoulders, posterior and lateral aspects of the neck, and lateral and posterior aspects of the head of the patient, and allowed to harden.

16 Claims, 5 Drawing Figures

KIT FOR AND METHOD OF IMMOBILIZING THE CERVICAL SPINE

BACKGROUND OF THE INVENTION

The human spinal column, when damaged, is vulnerable to significant additional damage if moved or manipulated prior to definitive medical intervention. Significant neurological deficits may result from movement of unstable injuries of the vertebral column from cord compression, shifting foreign bodies or bone fragments, or other aggravations of disrupted anatomy. The cervical spinal column is a commonly damaged part of the spinal column in industrialized countries, and damage in this area has the potential for the greatest permanent neurological sequalae. These injuries commonly result from automobile accidents, diving accidents and other forms of trauma. A key factor in proscribing damage to the spinal cord between the time of injury and definitive medical intervention is immobilization of the injured part. Standard equipment used to immobilize the cervical spinal column before definitive medical intervention consists of a variety of backboards, preformed cervical collars, braces, sandbags, straps, and various non-specific articles used in a makeshift manner. All of this equipment which defines the prior art, however, suffers from at least the following disadvantages to varying degrees:

(1) Many of the devices of the prior art do not adequately immobilize the cervical spine.

(2) Further movement or manipulations of the cervical spinal column are often necessary in order to position and place the equipment of the prior art.

(3) The equipment of the prior art sometimes provides suboptimal immobilization when the "fit" of the equipment changes with shifting of the patient's position and weight distribution, for example, in moving from a supine to upright position.

(4) The large size of many of the devices of the prior art can preclude their rapid utilization in certain special environments commonly encountered where their use is indicated, for example, within the close confines of automobile wreckage.

(5) Many devices of the prior art result in lost or significantly reduced therapeutic and/or diagnostic access to the anterior aspect of the neck. Likewise, these devices cannot be used on patients with tracheostomies in place.

(6) The devices of the prior art are unable to provide adequate immobilization of the cervical spine with the head and neck in any position other than neutral, a significant disadvantage in patients with certain conditions, for example ankylosing spondylitis, where the neurologic sequelae of fracture/dislocations may be exacerbated by attempts to stabilize the neck in a neutral position.

(7) The equipment of the prior art must be available in multiple sizes, that is, for adults, children and infants.

Although prior art devices for immobilizing the cervical spine have helped to reduce the morbidity and mortality associated with damage to the cervical spine, there is still much room for improvement. Accordingly, the present invention is directed to a new method of immobilizing the cervical spine and a kit which can be used in the method. This method is a significant improvement over the prior art, and does not suffer the disadvantages of the prior art.

SUMMARY OF THE INVENTION

The present invention describes a kit which contains two components to immobilize the cervical spine and a method for immobilizing the cervical spine. The first component comprises one or more straps wherein each strap has a first portion which engages certain body parts and a second portion which engages the second component such that the strap becomes anchored to the second component. In the preferred embodiment, the first component comprises at least two straps. However, it is also possible to utilize only one strap if injuries preclude the use of two straps. The second component is a substance which can be extruded from a container in a semisolid state and which can mold to the contours of objects before hardening into a rigid solid state. To immobilize the cervical spine in the preferred embodiment, the straps of the first component are held in place on, by way of example, the chin and forehead, while the second component is applied to the areas of the anterior, superior and posterior aspects of the shoulders, posterior and lateral aspects of the neck, and lateral and posterior aspects of the head of the patient, and allowed to harden.

The first component preferably comprises two straps. One strap is constructed to engage the chin by containing, for example, a chin cup. The second strap is constructed to engage the forehead by containing, for example, a headband. The remainder of the straps, excluding the chin cup, headband, or other modifications, contain slots, rings, appendages or other anchoring means which enable the second component to anchor the straps to the head and neck area.

The substance which comprises the second component may be a foamable plastic, resin, polymer or other substance which is non-toxic, x-ray lucent, moldable, non-flammable and rapidly hardens when extruded from a container.

DESCRIPTION OF THE PREFERRED EMBODIMENTS

The present invention overcomes the disadvantages of the prior art in the following ways:

(1) No movements or manipulations of the cervical spinal column are necessary in order to place the invention.

(2) The invention preserves diagnostic and/or therapeutic access to the anterior aspect of the neck.

(3) The invention can be used on patients with tracheostomies.

(4) Since the invention is molded to the contours of the patients individual body, an extremely close "fit" is obtained --resulting in a high quality of immobilization which will not be lost with shifting of the patient's position or weight distribution.

(5) The components of the invention can be made extremely compact, offering its ready placement in areas otherwise too confined for the prior art.

(6) The invention can immobilize the head and neck in any position.

(7) The capacity to treat dozens of patients can be stored within the space occupied by equipment of the prior art with the capacity to treat only a few patients, a factor which can be important for vehicles and rescue teams responding to mass casualty situations.

(8) The need to judge what size orthotic is needed for a particular patient, and to have that size available, is eliminated.

Figure 1A:
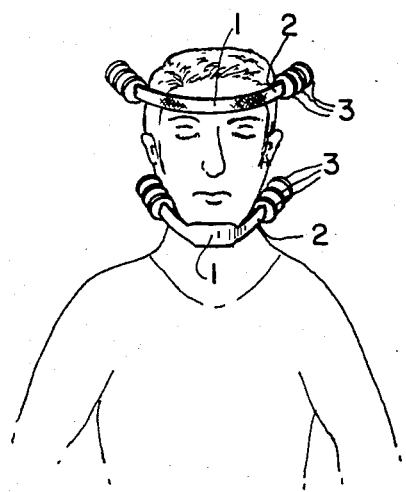
FIG. 1(a) is a front view of the head and neck area showing the positioning of the first component.
Figure 2A:
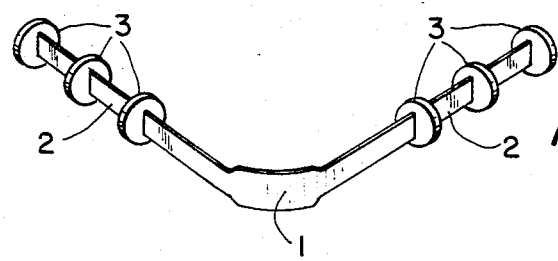
FIGS. 2(a) and 2(b) show the front and side view respectively of a strap having a body engaging portion and a portion having one type of appendage to engage the second component.
Figure 2B:
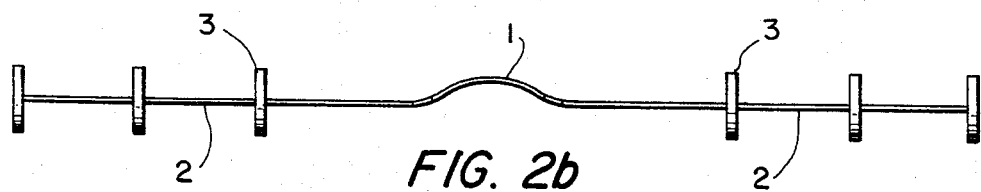

The first component comprises one or more straps. Each strap comprises two portions 1 and 2. The first portion 1 engages a body part in the head or neck area, for example, the chin or forehead. The second portion 2 is engineered to engage the second component such that the strap becomes anchored in it once the second component has hardened. Examples of portions of the strap which engage body parts include a chin cup 1 and headband 1', shown in FIG. 1(a). Any anchoring means 3 to which the second component can anchor the first component can be utilized in the second portion of the strap. Examples of the second portion of the strap include slots, rings and appendages. One type of anchoring means 3 is shown in FIGS. 2a and 2b. It is preferred that the first component comprises at least two straps. However, one strap may also be utilized if necessary, e.g. in view of injuries to the forehead or chin.

In order to be useful for the present invention, the second component should have the following properties:

(1) A composition such that the substance 4, when extruded from its container 5, is in a malleable form with the ability to mold to the contours of objects.

(2) A composition such that after molding to objects the substance 4 hardens to a rigid state. The more rapidly the substance 4 hardens, the more useful it is in the present invention.

(3) A suitable viscosity such that the substance 4 may be applied to vertical surfaces and remain there as a thick semisolid until hardening into a rigid state.

(4) A composition which is non-toxic.

(5) A composition which is non-flammable.

(6) A composition which is x-ray lucent.

As long as these requirements for the second component are met, the substance 4 of the second component could comprise a foamed plastic, foamed metal, resin, polymer or any similar substance known in the art. Examples of substances which could be used as a second component include copolymers of n-butyl acrylate and N-tert-butylacrylamide as described in U.S. Pat. No. 3,572,330, or polyurethane foams of the type described in U.S. Pat. No. 3,301,252. The hardening of the second component results in the anchoring of the first component in it and also the anchoring of the first component to the shoulders, head and neck of a person to which the invention has been applied.

Figure 1B:
FIG. 1(b) is the same view showing the application of the second component.
Figure 1C:
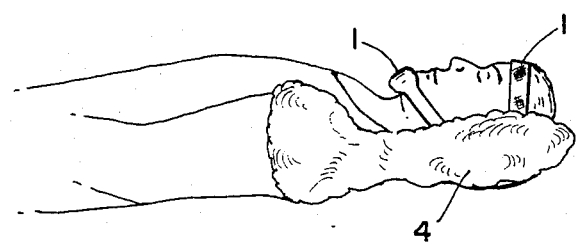
FIG. 1(c) is a side view after the first and second components have been applied.

The kit described above allows immobilization of the cervical spine according to the following sequence of placement of the invention. With the patient in, for example, the supine position, the chin strap and forehead strap of the first component are held in place with the second portions 2 of the straps lying freely alongside the lateral aspects of the head, FIG. 1(a). The second component is then extruded from its container 5 through a nozzle and directed to flow to the areas of the anterior, superior and posterior aspects of the shoulders as well as the posterior and lateral aspects of the neck and the lateral and posterior aspects of the head, making sure the substance interdigitates with the second portions 2 of the straps and its anchoring means 3 which are lying along the lateral aspects of the head, FIGS. 1(b) and 1(c). This distribution of the first and second components has been found to immobilize the cervical spine in all possible directions while at the same time preserving access to the anterior aspect of the neck. It has been found that the placement is easily accomplished without movement or manipulation of the patient's cervical spinal column. It will be obvious to those skilled in the art that the present kit allows immobilization of the cervical spinal column with the head and neck in any position, with only slight adjustments in the placement of the invention. The patient can be in any position, e.g. supine, sitting, trapped within wreckage, etc., and the present invention can be applied to completely immobilize the cervical spine.

The foregoing disclosure and description of the invention are illustrative and explanatory thereof, and various changes in the size, shape and materials as well as in the details of the illustrated construction may be made without departing from the spirit of the invention.

What is claimed is:

1. A kit for immobilizing the cervical spine comprising a first component and a second component, said first component comprises one or more straps wherein each strap is of sufficient length to extend alongside the lateral aspects of the head and comprises a first portion which engages a body part of the head or neck area, and a second portion capable of lying alongside said lateral aspects of the head and having means for anchoring said first component to said second component, and said second component comprises a substance which can be extruded from a container in a semisolid state and which can mold to the contours of the anterior, superior and posterior aspects of the shoulders, the posterior and lateral aspects of the neck, and the lateral and posterior aspects of the head, before hardening into a rigid solid state.

2. The kit of claim 1, wherein said first component comprises at least two straps.

3. The kit of claim 1 wherein said first component comprises a first strap for engaging the chin and a second strap for engaging the forehead.

4. The kit of claim 2, wherein said first component comprises a first strap for engaging the chin and a second strap for engaging the forehead.

5. The kit of claim 3 wherein said first portion of said first strap is a chin cup and said first portion of said second strap is a headband.

6. The kit of claim 4 wherein said first portion of said first strap is a chin cup and said first portion of said second strap is a headband.

7. A method of immobilizing the cervical spinal column which comprises placing a first component comprising one or more straps about the head, holding the straps in position, extruding a second component comprising a substance in a semisolid state about the anterior, superior, and posterior aspects of the shoulders, the posterior and lateral aspects of the neck, and the lateral and posterior aspects of the head, including the distal segments of the straps, and allowing said substance to harden into a rigid solid state, whereby said first component becomes anchored in said substance and to said shoulder, head and neck, thereby immobilizing the cervical spine.

8. The method of claim 7 wherein each strap of said first component comprises a first portion for engaging a body part of the head or neck area and a second portion for engaging said second component.

9. The method of claim 7 wherein said first component comprises at least two straps.

10. The method of claim 9 wherein each strap of said first component comprises a first portion for engaging a body part of the head or neck area and a second portion for engaging said second component.

11. The method of claim 8 wherein said second portion contains means for anchoring said first component to said second component.

12. The method of claim 10 wherein said second portion contains means for anchoring said first component to said second component.

13. The method of claim 11 wherein said first component comprises a first strap for engaging the chin and a second strap for engaging the forehead.

14. The method of claim 12 wherein said first component comprises a first strap for engaging the chin and a second strap for engaging the forehead.

15. The method of claim 13 wherein said first portion of said first strap is a chin cup and said first portion of said second strap is a headband.

16. The method of claim 14 wherein said first portion of said first strap is a chin cup and said first portion of said second strap is a headband.

* * * * *